United States Patent [19]

Velasquez Urey

[11] Patent Number: 5,455,111
[45] Date of Patent: Oct. 3, 1995

[54] CONSTRUCTION ADHESIVE FOR POROUS FILM

[75] Inventor: Ruben E. Velasquez Urey, Lake Elmo, Minn.

[73] Assignee: Minnesota Mining and Manufacturing Company, St. Paul, Minn.

[21] Appl. No.: 226,653

[22] Filed: Apr. 12, 1994

[51] Int. Cl.$^6$ ...................................................... C09J 7/02
[52] U.S. Cl. .................... 428/315.5; 428/317.1; 428/317.3; 428/317.7; 428/355
[58] Field of Search ..................... 428/343, 355, 428/315.5, 315.9, 317.1, 317.3, 317.7

[56] References Cited

U.S. PATENT DOCUMENTS

| | | | |
|---|---|---|---|
| 3,362,940 | 1/1968 | Edwards et al. | 260/88.2 |
| 3,573,240 | 3/1971 | Flanagen et al. | 260/23 |
| 4,100,238 | 7/1978 | Shinomura | 264/49 |
| 4,247,498 | 1/1981 | Castro | 264/41 |
| 4,361,672 | 11/1982 | Agarwal et al. | 525/54.5 |
| 4,451,589 | 5/1984 | Morman et al. | 523/124 |
| 4,539,256 | 9/1985 | Shipman | 428/315.5 |
| 4,554,304 | 11/1985 | Hansen et al. | 524/291 |
| 4,568,713 | 2/1986 | Hansen et al. | 524/291 |
| 4,609,584 | 9/1986 | Cutler | 428/156 |
| 4,726,989 | 2/1988 | Mrozinski | 428/315.5 |
| 4,734,447 | 3/1988 | Hattori et al. | 524/271 |
| 4,824,718 | 4/1989 | Hwang | 428/284 |
| 4,824,889 | 4/1989 | Mostert | 524/232 |
| 4,902,553 | 2/1990 | Hwang | 428/156 |
| 4,937,138 | 6/1990 | Mostert | 428/286 |
| 4,939,202 | 4/1990 | Maletsky et al. | 524/528 |
| 4,998,928 | 3/1991 | Maletsky et al. | 604/365 |
| 5,041,492 | 8/1991 | Koprowicz et al. | 524/274 |
| 5,256,717 | 10/1993 | Stauffer et al. | 524/293 |
| 5,266,394 | 11/1993 | Diehl et al. | 428/261 |

FOREIGN PATENT DOCUMENTS

| | | | |
|---|---|---|---|
| 33060/89 | 4/1989 | Australia | C09J 3/14 |
| 0201996A2 | 3/1986 | European Pat. Off. | C88L 23/10 |

*Primary Examiner*—Jenna L. Davis
*Attorney, Agent, or Firm*—Gary L. Griswold; Walter N. Kirn; William J. Bond

[57] ABSTRACT

There is provided a laminate of a liquid additive containing microporous film with a hot-melt adhesive composition. The hot-melt adhesive is formulated with polybutylene polymers or copolymers with optional tackifiers and/or plasticizers such that the microporous film in the areas of adhesive contact has an L value of at least 70, most preferably at least 80. The liquid additive is preferably a plasticizing oil such as mineral oil.

28 Claims, 1 Drawing Sheet

CONSTRUCTION ADHESIVE FOR POROUS FILM

BACKGROUND AND FIELD OF THE INVENTION

The present invention relates to hot-melt construction adhesives for adhering thermoplastic porous films to a substrate.

Typically, disposable absorbent articles require an outer liquid impermeable polymeric film or backsheet to prevent absorbed liquid from passing through the article into contact with the wearers clothing or skin. As this liquid impermeable film layer is typically not breathable, not allowing passage of moisture vapor, the articles can become hot and uncomfortable and occasionally lead to skin rashes. In this regard, liquid impermeable microporous film has been proposed to make the absorbent article breathable. A common disposable microporous film is filled with particulate fillers in amounts greater than about 30 percent. However, these breathable particulate filled films are less desirable in terms of softness and feel and contamination to the tape.

U.S. Pat. No. 4,902,553 proposes a rattle free vapor permeable microporous polymeric film for use as a outer liquid impermeable backsheet for a disposable absorbent product such as a diaper or an incontinent product. This patent proposes using a liquid impermeable but vapor permeable microporous film, which would allow moisture vapor to escape reducing the tendency for the absorbent product to cause a rash, such as diaper rash or other types of skin irritation. The microporous film is a soft, rattle-free, vapor permeable, liquid impermeable film. The rattle free nature of the film is accomplished by inclusion of rattle reducing liquid additive materials in the film and by embossment. Other patents describing liquid additive containing microporous films include U.S. Pat. Nos. 4,539,256; 4,609,584; 4,726,989 or 4,824,719. The microporous films described in these patents are all well suited for use as a microporous liquid impermeable film in a hygienic or absorbent article. However, a problem with these films is that the films have a tendency to change from opaque to translucent at points of hot-melt adhesive contact. This is particularly noticeable and objectionable when the films are adhered to a substrate with conventional hot-melt adhesives in an intermittent adhesive pattern. This results in an aesthetically displeasing product that also has a weakened level of adhesion between the microporous film and the substrate. This is a particular problem when the liquid additive is a plasticizing oil, such as mineral oil. Although numerous formulations of conventional hot-melt pressure sensitive adhesives have been evaluated by the applicant to adhere these microporous films to conventional substrates all have uniformly resulted in clearing the film at the points of adhesive contact. This film clearing also tends to spread to adjacent areas of the film not in direct contact with the adhesive. After an extensive investigation and screening the Applicants have discovered adhesives which address the problems identified above particularly with respect to the above liquid additive containing microporous films.

BRIEF DESCRIPTION OF THE INVENTION

Figure 1:
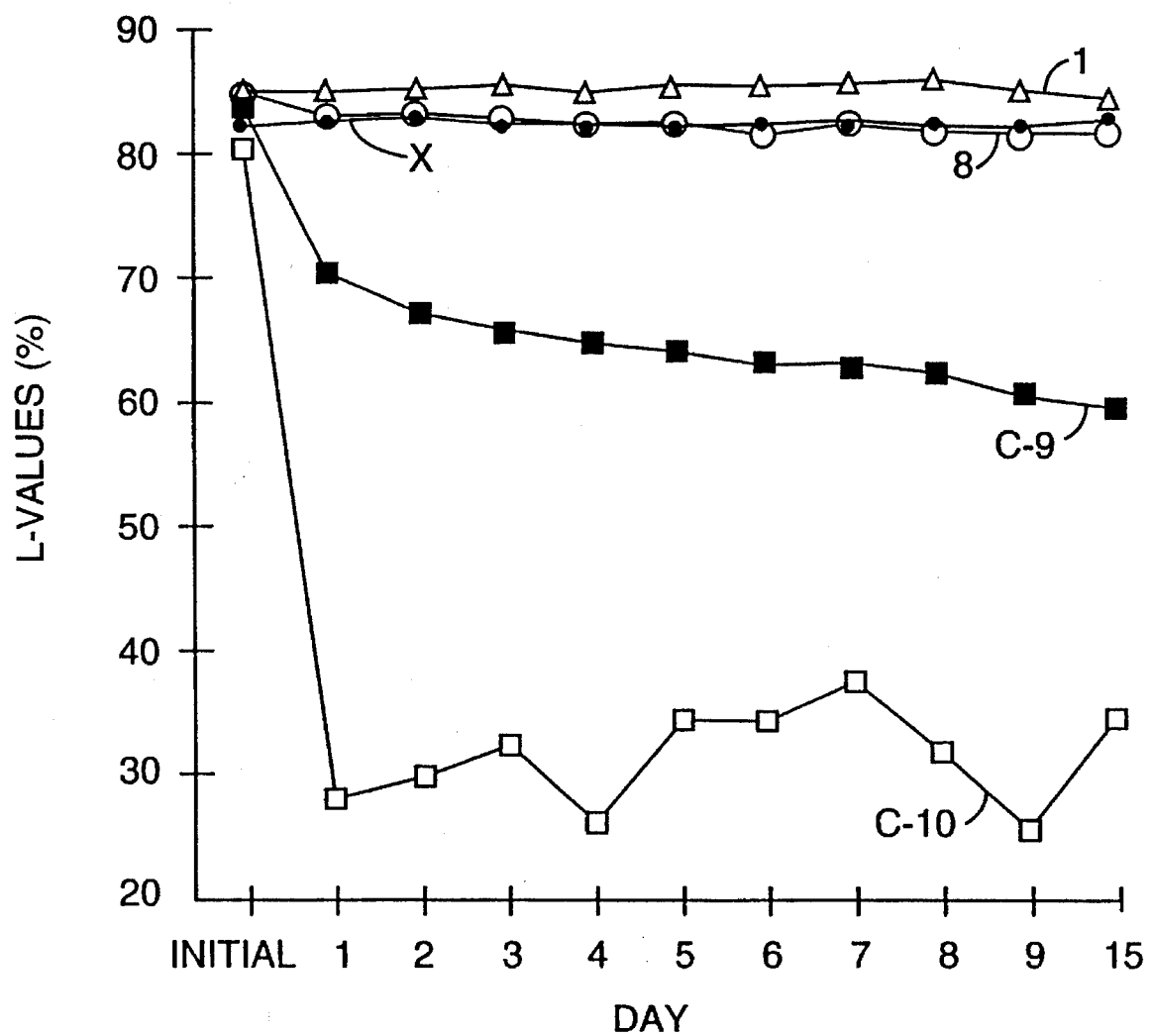
FIG. 1 is a graph comparing the performance of the invention adhesives to prior art adhesives.

The present invention provides a laminate of a microporous film, preferably containing a liquid additive such as a plasticizing oil, which is adhered to a substrate, such as an absorbent pad, by an improved hot-melt adhesive composition, particularly well suited for multi-line or intermittent adhesive application, without clearing of the microporous film.

The invention laminate uses a hot-melt adhesive composition based on a crystalline thermoplastic polymer providing a hot melt adhesive having an open time of at least 5 seconds and preferably more than 1 minute. The hot melt adhesive preferably comprises 100 parts polybutylene, polybutylene copolymer or blends thereof, 0 to 300 parts of a compatible solid tackifying resin, 0 to 40 parts a plasticizer, and optionally 0 to 50 parts of a filler and 0 to 15 parts of a polymer viscosity reducing additive.

DESCRIPTION OF THE PREFERRED EMBODIMENTS

The hot-melt adhesive of the invention laminate provides high shear and peel adhesion to microporous films, particularly a liquid additive containing microporous film such as described in U.S. Pat. Nos. 4,902,553; 4,539,256; 4,609,584; 4,726,989; or 4,824,718, without causing the film(s) to clear or turn from opaque to translucent. A microporous film in the laminate having an L value of at least 80 maintains an L value of at least 70, preferably at least 75 and most preferably at least 80, after 15 days of heat aging, at the points of adhesive contact with the hot-melt adhesive and in areas adjacent to the points of adhesive contact. The T-peel adhesion of the microporous film to a substrate in the laminate is at least 20 g/25 mm, and preferably at least 50 g/25 mm, with 2,000 grams of rolldown application and 15 days heat aging.

The preferred liquid additive containing microporous film in the laminate, described in the above patents, comprises a microporous film formed by dissolving a crystallizable polymeric material in a liquid additive at a temperature above the melt temperature of the polymeric material and forming this melt into a film, such as by extrusion. The homogeneous solution is then permitted to cool at a rate suitable to cause the crystallizable polymer to crystallize into a distinct interconnected phase, the polymer being incompatible with the additive at ambient or use conditions. The phase-distinct film material is then uniaxially or multiaxially orientated, creating a film with micropores, which pores contain the now phase-distinct liquid additive. The liquid additive is preferably one which exhibits plasticizing properties. Potential additive materials include saturated hydrocarbons such as mineral oil, glycerin, petroleum jelly, low molecular weight polyethylene, polyethylene oxide, polypropylene oxide, polytetramethylene oxide, soft carbowax, plasticizing oils, and the like. Preferred additive materials are plasticizing oils, with mineral oil being particularly preferred because of its relatively low cost and excellent film-forming properties. The crystallizable polymeric material is preferably olefinic, such as polyolefins, or condensation polymers such as polyesters or polyamides. Most preferred are polyolefins such as crystalline isotactic polypropylene, polyethylene, polybutylene, polyethylpentene, copolymers, block polymers and modified versions thereof.

The additive liquid can be used in an amount ranging from about 5 to 80 percent by weight of the formed film, preferably 5 to 50 percent, and most preferably 10 to 30 percent.

Discussions of crystallizable polymers and phase-separating additives are also found in U.S. Pat. Nos. 4,247,498 and 4,100,238. For example, for isotactic polypropylene, these patents describe the use of phase-separable additives such as poly-1-butene, polyethylene wax, low molecular weight polyethylene, alcohols, aldehydes, amines, esters such as methylene benzoate, ethers such as diphenylether, hydrocarbons such as trans-stilbene or ketones.

Nucleating agents such as those described in U.S. Pat. Nos. 4,824,718 and 4,726,989 can also be used to produce uniform crystallization of the polymeric material upon cooling. These nucleating agents preferably are at least a primary agent, generally an organic acid or derivative, which dissolves in the liquid additive at a temperature at least more than 10° C. above the crystalline transition temperature of the thermoplastic polymer, and which is used in amounts from 0.05 to 5 percent by weight of the system, and optionally a secondary inert nucleating agent, which is employed in approximately the same concentration. The secondary inert nucleating agent normally comprises an inorganic particulate material such as talc, titanium dioxide, calcium carbonate, magnesium carbonate, barium carbonate, magnesium sulfide, barium sulfide, and the like. Suitable organic acids include mono- or polyacids, e.g., carboxylic acids, sulfonic acids, phosphonic acids, and solid organic alcohols such as dibenzylidene sorbitol. The preferred organic acids include adipic acid and succinic acid, and a preferred secondary nucleating agent is talc.

Following precipitation of the thermoplastic crystallizable polymer, the film can be used, unoriented or orientated, with a stretch ratio in at least one direction of 0 to 3, preferably from 1.5 to 2.5. When the film is not oriented, the liquid additive is preferably washed from the film.

Generally, the thickness of the microporous film is from 5 to 250 microns, preferably from 20 to 200 microns. Comparatively thinner films are preferred in terms of cost and increased moisture vapor permeability. Thicker films provide improved tensile performance against more aggressive adhesives.

The hot-melt adhesive polymer is a crystalline thermoplastic polymer which when applied as a hot-melt, optionally as a polymer blend, and with any added tackifying resins, plasticizers or other additives, generally will tend to provide an adhesive having a tackiness open time of at least 5 seconds, more often greater than 1 minute, most likely more than 5 minutes. For conventional hot melt spray adhesive application the adhesive viscosity is preferable less than 10,000 centipoise (cp), most preferably less than 5,000 cp. For extrusion application such as by melt blowing the adhesive viscosity can be as high as 50,000 cp or more.

The crystalline thermoplastic polymer is preferably a homopolymer or copolymer of 1-butene or a blend thereof. Preferred is a copolymer of 1-butene with 1–30 mole percent of a comonomer of an alpha olefin, preferably polyethylene, polypropylene, 2-butene, or a $C_5$ to $C_8$ alpha olefin. The comonomer is preferably in a mole percent of between 2 and 15 percent based on the entire polymer with the preferred comonomer being an ethylene monomer. These polymers and copolymers are discussed in U.S. Pat. No. 4,937,138. Amorphous polymers (e.g., polypropylene, polyhexene and polyoctene) provide adhesives that clear the microporous film.

The tackifying components for the crystallizable polymer based adhesives generally comprise solid tackifying resin used alone or in combination with a liquid tackifying resin and/or a liquid plasticizer. Preferably, the tackifying resin is selected from the group of resins at least partially compatible with the elastomeric polymer or block copolymer. Such tackifying resins include those aliphatic hydrocarbon resins made from the polymerization of a feed stream consisting mainly of unsaturated species containing 4 to 6 carbon atoms; rosin esters and rosin acids; mixed aliphatic/aromatic tackifying resins; polyterpene tackifiers; and hydrogenated tackifying resins. The hydrogenated resins can include resins made from the polymerization and subsequent hydrogenation of a feed stock consisting mainly of dicyclopentadiene; resins produced from the polymerization and subsequent hydrogenization of pure aromatic feed stocks, such as styrene; resins produced from the polymerization and subsequent hydrogenation of an unsaturated aromatic feed stream, wherein the feed stream consists mainly of species containing 7 to 10 carbon atoms; hydrogenated polyterpene resins; and hydrogenated aliphatic and/or aliphatic/aromatic resins. Preferred tackifying resins include the aliphatic hydrocarbon resins and the hydrogenated resins. Although not preferred, generally, a relatively minor portion of the tackifying resin can include resins not compatible with the crystalizable polymer, generally formed from aromatic species. The solid tackifying resins are preferable used in amounts from 2 to 150 parts to each 100 parts of the crystallizable polymer, most preferably 5 to 100 parts.

Suitable plasticizers for use in the laminate hot-melt adhesive composition include the phase-separable additives in the liquid additive containing microporous film including waxes such as petroleum waxes, Fischer-Tropsch waxes, microcrystalline waxes, polyolefin waxes, and plasticizer oils such as naphthionic oils, paraffinic oils, aromatic oils, polybutene oil and mineral oils. Either the waxes or the plasticizer oils or other plasticizers can be used in amount up to 40 parts for 100 parts of the crystallizable polymer. Preferably lower molecular weight plasticizers (less than 500 average MW) or having a significant proportion of liquid species at temperatures less than 50° C., such as plasticizing oils or paraffin wax or liquid tackifiers, are used at levels of less than 20 parts to 100 parts polymer. Preferably, higher molecular weight (greater than 1000 average MW) or having very little liquid species at less than 50° C., such as waxes, or higher melting point plasticizers are used at levels of less than 35 parts to 100 parts polymer.

Some waxes and/or plasticizers can be added to reduce the viscosity of the adhesive to a preferred range. Molecular weight, or polymer viscosity, reducing additives such as free fradical initiators like peroxides (e.g., 2,5-dimethyl 2,5-bis(t-butyl peroxy)hexyne-3) or transition metal catalysts and the like can also be added to the polymer, preferably in amounts of from 0.01 to 50 parts to 100 parts polymer, most preferably 0.01 to 5 parts.

Fillers can be added to the adhesive formulation to increase the opacity or L value of the microporous film at the points of adhesive contact. Fillers are particularly useful for lower viscosity hot melt adhesives of the invention, which tend to slightly reduce the L value of the microporous film at the points of adhesive contact, but not in adjacent areas of the microporous film. Useful fillers include the particulates used for the particle filled microporous film, titanium dioxide is preferred in terms of cost and opacity. Preferably the fillers are used in amounts ranging from 0 to 25 parts to 100 parts polymer, most preferably less than 15 parts.

It is also contemplated that nucleating agents can be added to the preferred adhesive formulation in small amounts to increase crystallization and the crystallization rate. Such nucleating agents would include isotactic polypropylene, stearamide or 1-naphthaleneacetamide in amounts ranging from 0.01 to 10 parts, preferably 0.1 to 5 parts, most preferably less than 1 part, based on the overall adhesive formulation. Other nucleating agents known in the art are described in U.S. Pat. No. 4,937,138.

The preferred polybutylene copolymer can be used in a blend with polybutylene homopolymer, preferably in a range of 1/10 to 10/1 polymer to copolymer, more preferably in a ratio of 2/10 to 10/2.

The polybutylene copolymers can also be modified by incorporating functional monomers or subsequently grafting with moieties such as maleic anhydride or other free radically reactive modifying agents.

The microporous film adhesive laminate will generally further comprise a substrate layer which will eventually be a breathable web or other material including conventional nonwoven webs such as spun bond, spun lace, melt-blown, carded or otherwise formed nonwoven webs, woven fabrics, papers or absorbent batts where the laminate construction is a component in a disposable absorbent product such as a diaper, feminine hygiene pad or adult incontinent product. In a preferred embodiment, the laminate is point or pattern embossed by heat, pressure, ultrasonics, or the like. Embossing softens the feel of the laminate while partially masking any slight clearing of the film.

Examples 1–8 and 11–18

The adhesive samples A–Q (except for adhesive H) were melted and knife-coated onto the microporous film to the thicknesses indicated in Tables III and IV. The microporous film used was prepared in accordance with U.S. Pat. Nos. 4,539,256 and 4,726,989. The microporous film composition was 70 weight percent polypropylene (#5D45, 0.65 MFI polypropylene available from Shell Chemical Co.), 29.9 weight percent mineral oil (Amoco White #31 USP Grade, available from Amoco Oil Co.), and 0.1 weight percent dibenzylidine sorbitol nucleating agent (Millad 3905, available from Milliken Chemical). The microporous film thickness was approximately 1.8 mil (45 microns). The samples tested and the opacity data obtained are summarized in Tables III and IV. In FIG. 1 the opacity values of examples 1 and 8, comparative examples 9 and 10 and a base film x are graphically displayed with the film heat aged to 15 days at 50° C.

Comparative Examples 9 and 10

For comparison, two commercially available hot melt adhesives were evaluated. Ecomelt #H-406, and National Starch #34-5566 (both styrene-butadiene copolymer adhesives tackified with a hydrocarbon type tackifier), were coated onto the microporous film in a manner similar to that described above. The opacity data obtained for these comparative examples are summarized in Table III.

TABLE I

| Component | A | B | C | D | E | F | G | H | I |
|---|---|---|---|---|---|---|---|---|---|
| DP 8910PC | 100 | 98 | 97 | 85 | 85 | 85 | 78 | 49 | 87 |
| "IRGANOX" 1076 | — | 2 | 2 | — | — | — | 2 | 2 | 2 |
| "ARKON" P-100 | — | — | — | 10 | 10 | 10 | 10 | 10 | 10 |
| "LUPERCO" 101-XL | — | — | 1 | — | — | — | — | — | 1 |
| "MEKON" | — | — | — | 5 | — | — | — | — | — |
| "UNILIN" 700 | — | — | — | — | 5 | — | — | — | — |
| "POLYWAX" 2000 | — | — | — | — | — | 5 | 10 | 39 | — |
| Brookfield viscosity[1] (cp) | 7500 | 8530 | 3600 | 7970 | 6300 | 6600 | 8780 | 3675 | 3925 |

[1]Measured at 170° C. after at least 1 hour heating, using a Brookfield digital viscometer model #DV-I according to ASTM #D2556.

Adhesive Preparation

Adhesives were prepared by pre-blending the adhesive components, feeding them into a single screw extruder and mixing/melting the blend at temperatures of at least 350° F. (177° C.). The adhesive samples were collected in a tin tray and were later cut into small pieces which were then used for hot melt spraying. The adhesive compositions that were evaluated are summarized in Tables I and II. Brookfield viscosity data is reported for the adhesives in Table I.

TABLE II

| Component | J | K | L | M | N | O | P | Q |
|---|---|---|---|---|---|---|---|---|
| DP 8910PC | 78 | 73.5 | 69 | 49 | 88 | 78 | 69 | 88.7 |
| "IRGANOX" 1076 | 2 | 2 | 2 | 2 | 2 | 2 | 2 | 1 |
| "ARKON" P-100 | 20 | 24.5 | 29 | 49 | — | — | — | — |
| "PICCOLYTE" S-115 | — | — | — | — | 10 | 20 | 29 | — |
| "ESCOREZ" 5300 | — | — | — | — | — | — | — | 9.9 |
| "LUPERCO" 101-XL | — | — | — | — | — | — | — | 0.4 |

TABLE III

| Example | Adhesive Type | Adhesive Thickness (microns) | L Value (%) Initial | L Value (%) 1 Day Heat Aged | L Value (%) 3 Day Heat Aged | L Value (%) 5 Day Heat Aged | L Value (%) 7 Day Heat Aged | L Value (%) 9 Day Heat Aged | L Value (%) 15 Day Heat Aged |
|---|---|---|---|---|---|---|---|---|---|
| 1 | A | 48 | 84.62 | 84.25 | 84.96 | 84.52 | 84.65 | 83.97 | 83.51 |
| 2 | B | 56 | 84.11 | 84.25 | 84.43 | 84.12 | 84.16 | 84.03 | 83.39 |
| 3 | C | 58 | 84.62 | 84.25 | 84.23 | 83.61 | 83.38 | 82.93 | 83.22 |
| 4 | D | 38 | 84.11 | 82.68 | 82.22 | 79.71 | 79.28 | 78.88 | 79.83 |
| 5 | E | 53 | 84.42 | 84.72 | 84.55 | 84.42 | 84.11 | 83.77 | 83.39 |
| 6 | F | 43 | 84.63 | 83.91 | 83.71 | 82.90 | 82.84 | 82.53 | 82.35 |

TABLE III-continued

| Example | Adhesive Type | Adhesive Thickness (microns) | L Value (%) Initial | L Value (%) 1 Day Heat Aged | L Value (%) 3 Day Heat Aged | L Value (%) 5 Day Heat Aged | L Value (%) 7 Day Heat Aged | L Value (%) 9 Day Heat Aged | L Value (%) 15 Day Heat Aged |
|---|---|---|---|---|---|---|---|---|---|
| 7 | G | 41 | 84.22 | 84.08 | 83.84 | 83.46 | 82.93 | 82.79 | 82.33 |
| 8 | I | 46 | 84.70 | 83.31 | 82.51 | 81.89 | 81.52 | 80.74 | 80.49 |
| C9 | ECOMELT H-406 | 38 | 84.01 | 70.14 | 65.38 | 63.71 | 62.08 | 59.97 | 58.84 |
| C10 | N.S. #34-5566 | 38 | 80.22 | 27.48 | 31.62 | 33.40 | 36.52 | 24.45 | 33.32 |

TABLE IV

| Example | Adhesive Type | Adhesive Thickness (microns) | L Value (%) Initial | L Value (%) 1 Day Heat Aged | L Value (%) 2 Day Heat Aged | L Value (%) 3 Day Heat Aged | L Value (%) 6 Day Heat Aged | L Value (%) 7 Day Heat Aged |
|---|---|---|---|---|---|---|---|---|
| 11 | J | 81 | 84.14 | 84.36 | 83.53 | 83.46 | 81.75 | 81.55 |
| 12 | K | 69 | 83.46 | 83.31 | 82.98 | 82.64 | 80.39 | 80.56 |
| 13 | L | 43 | 83.95 | 83.10 | 82.00 | 81.37 | 80.17 | 79.66 |
| 14 | M | 66 | 84.53 | 84.75 | 84.14 | 83.62 | 82.34 | 82.01 |
| 15 | N | 61 | 84.36 | 84.29 | 84.11 | 83.46 | 82.88 | 82.47 |
| 16 | O | 25 | 83.97 | 83.52 | 82.88 | 82.37 | 81.46 | 80.97 |
| 17 | P | 69 | 84.70 | 84.62 | 83.89 | 83.69 | 82.73 | 82.58 |
| 18 | Q | 66 | 84.62 | 84.57 | 84.55 | | 84.38 | |

Examples 19–32

Approximately 1000 grams of the adhesive was melted at 330° F. (166° C.) in the melt tank of a hot melt adhesive sprayer (Nordson 3500 Series, available from Nordson Corp.) and was then sprayed through a 0.012 inch (0.305 mm) diameter nozzle onto to the microporous film substrate (of Examples 1–18) creating a spiral adhesive pattern on the film that was approximately one inch (2.54 cm) in width. Three rows of the adhesive were coated in the longitudinal or machine direction of a six inch (15.2 cm) wide sample of the microporous film. The rows of the adhesive were separated by approximately inch (2.54 cm) wide areas of non-adhesive coated regions.

A nonwoven fabric was then immediately placed on top of the adhesive surface by hand and the microporous film/adhesive/nonwoven laminate was then rolled down by hand with two passes using a 4.5 pound (2 kg) rubber roller. The nonwoven fabric used was typical of that used for the inner topsheet of a disposable diaper, a point-bonded spunbond polypropylene having a basis weight of 0.8 oz/yard$^2$ (25.8 gms/m$^2$) (available from International Paper Co.).

The laminates were tested for initial and heat aged (at 50° C.) T-peel adhesion. Initial T-peel adhesion means that the samples were tested within three days of preparing the laminates. The results are summarized in Table V.

Comparative Examples 33–35

For comparison several amorphous polyalphaolefin polymers were evaluated. The polymers evaluated were a propylene homopolymer ("REXTAC™" 2115 available from Rexene Products Co.), an ethylene-propylene copolymer ("REXTAC™" 2304 available from Rexene Products Co.), and a butene-propylene copolymer ("REXTAC™" 2715 available from Rexene Products Co.). These polymers have heats of crystallization of 25, 15, and 6 Joules/gm, respectively, compared to isotactic polypropylene which has a heat of crystallization of 95–100 Joule/gm.

The polymers were melted in the sample chamber of a hand held hot melt adhesive spray gun and were sprayed in a spiral pattern onto microporous film samples identical to those used in examples 1–18. A nonwoven fabric identical to that used in the examples 1–18 was then immediately placed on top of the adhesive surface by hand. For all three samples the microporous film turned clear where it had come into contact with the amorphous polymers.

TABLE V

| Example | Adhesive Type | T-Peel Adhesion Initial | T-Peel Adhesion 1 Day HA | T-Peel Adhesion 3 Day HA |
|---|---|---|---|---|
| 19 | A | 225 | 147 | 143 |
| 20 | B | 189 | 98 | 88 |
| 21 | C | 69 | 123 | 130 |
| 22 | D | 151 | — | 274 |
| 23 | E | 164 | 130 | 104 |
| 24 | F | 178 | — | 177 |
| 25 | G | 184 | 178 | 157[1] |
| 26 | H | 20 | — | 16 |
| 27 | I | 139 | 307 | 260 |
| 28 | J | 180 | 187 | — |
| 29 | K | 128 | — | 223 |
| 30 | N | 260 | 250 | — |
| 31 | O | 273 | 318 | — |
| 32 | Q | 333 | 359 | 387[2] |

[1]sample was heat aged for 4 days
[2]sample was heat aged for 2 days

Comparative Example 36

The adhesive of comparative example 9 ("ECOMELT" H-406) was melted in a tank and blended with a blue particulate color concentrate to determine if the color in the adhesive would hide the clearing effect that occurs with a conventional adhesive. The adhesive blend was pattern coated onto the porous film of examples 1–18 using dot patterns with coverages ranging from 12.5% to 50% of the total surface of the film, and subsequentally hand laminated with a nonwoven. The resulting laminate started clearing the film after 2–3 days at room temperature. Although the adhesive dots maintained their color through the film, the rest of the film, the areas not coated with adhesive, turned clear with clearing spreading from the adhesive contact points outward. The addition of the particles did not solve the problem of microporous film clearing when using conventional adhesives.

Example 37

A polybutylene based hot-melt adhesive of the formulation;

DP-8910 65%,

Arkon P-100 10%, and

Polybutene oil (Indapol #H-1900) 20% was heated and degraded until it turned to light brown. This was done to lower the viscosity of the adhesive so as to cause slight clearing of a microporous film. After being degraded, 5% of $TiO_2$ was added to see if the $TiO_2$ would hide any clearing of the porous film after spray coating and heat aging. The adhesive coated film was laminated onto a nonwoven substrate as with all the previous samples. Although the resulting laminate showed a slight discoloration of the film right over the glue lines, there was no discoloration beyond the glue line.

DP 8910PC is a polybutylene/polyethylene copolymer (6% ethylene content) having 34% crystallinity as measured by wide angle X-ray, available from Shell Chemical Co.

"IRGANOX™" 1076 is a hindered phenol antioxidant available from Ciba-Geigy.

"ARKON™" P-100 is a hydrogenated C9 solid tackifying resin available from Arakawa Chemical Co.

"PICCOLYTE™" S-115 is a beta pinene solid tackifying resin available from Hercules Inc.

"ESCOREZ™" 5300 is a hydrogenated hydrocarbon solid tackifying resin available from Exxon Chemical.

"LUPERCO™" 101-XL is a peroxide available from Elf Atochem North America Inc.

"MEKON™" is a white microcrystalline petroleum based wax available from Petrolite.

"UNILIN™" 700 is a saturated, long chain, linear alcohol available from Petrolite.

"POLYWAX™" 2000 is a polyethylene wax having a Mn=2000 and a melting point of 126° C. available from Petrolite.

"INDAPOL™" H=1900 is a polybutene oil available from Amoco.

TEST METHODS

The following tests were used to evaluate the polybutylene-based construction adhesives for microporous film.

T-Peel Adhesion Test

The test was carried out at constant temperature and humidity (23° C. and 50% relative humidity) and the microporous film/nonwoven laminate samples were conditioned for 24 hours prior to testing. A 1"×6" (2.5 cm×12.7 cm) sample of the laminate cut in the transverse or cross direction of the laminate was used for testing. Each test sample was cut such that at least one end of the test piece was free of adhesive. The nonwoven layer was then placed in the lower jaw of a constant rate "INSTRON™" tensile tester and the microporous film layer was placed in the upper jaw of the tensile tester. At a crosshead speed of 12 inches (30.5 cm) per minute the force required to peel the microporous film from the nonwoven in a T-peel mode (180 degrees) was recorded. The force required to remove the film from the nonwoven is reported in grams/25 mm width and the reported values are an average of at least six tests (two test samples having three separate adhesive regions).

Opacity Test

The opacity, or white component, of the adhesive coated microporous film was measured in order to evaluate the clearing effect of the adhesive on the microporous film. The opacity can be described in terms of its L value from the LAB color test. The L values were measured using a "LABSCAN™" Spectro Colorimeter (Hunter Associates Laboratory, Inc., Reston, Va.) using TAPPI test procedure #T-524. Initial and heat aged (up to 7–15 days at 50° C.) data were obtained. The values reported are an average of two tests.

The various modifications and alterations of this invention will be apparent to those skilled in the art without departing from the scope and spirit of this invention, and this invention should not be restricted to that set forth herein for illustrative purposes.

I claim:

1. A laminate structure comprising a liquid additive containing microporous thermoplastic film, a continuous or intermittent hot-melt adhesive coating layer where the liquid additive containing microporous film at the points of adhesive contact has an L value of at least 70, the hot-melt adhesive comprising;

100 parts of a polybutylene polymer or copolymer or blend, wherein the copolymer comprises 1 to 30 mole percent of a comonomer of a $C_2$ to $C_3$, or $C_5$ to $C_8$ alpha olefin, 0 to 300 parts of a solid tackifying resin compatible with the polybutylene phase, 0 to 20 parts of a liquid tackifier, 0 to 40 parts of a plasticizer and 0 to 25 parts of a particulate filler.

2. The laminate of claim 1 wherein the hot-melt adhesive has a tack open time of at least 5 seconds.

3. The laminate of claim 1 wherein the microporous thermoplastic film layer liquid additive forms a distinct phase within the microporous film.

4. The laminate of claim 3 wherein the liquid additive comprises 5 to 50 percent by weight of the film, and the microporous film is oriented.

5. The laminate of claim 4 wherein the liquid additive comprises 10 to 30 percent by weight of the film, and the microporous film is oriented by up to 3:1 in at least one direction.

6. The laminate of claim 5 wherein the liquid additive is selected from plasticizing oil, glycerin, petroleum jelly, soft carbowax, low molecular weight polyethylene, polyethylene oxide, polypropylene oxide, polytetramethylene oxide or mixtures thereof.

7. The laminate of claim 6 wherein the liquid additive is mineral oil.

8. The laminate of claim 3 wherein the hot-melt adhesive has an open time of at least 1 minute further comprises 0.01 to 10 parts of a polymer viscosity reducing additive.

9. The laminate of claim 7 wherein the hot-melt adhesive composition has a viscosity of less than 10,000 cp.

10. The laminate of claim 9 wherein the hot-melt adhesive composition has a viscosity of less than 5,000 and an open time of greater than 5 minutes.

11. The laminate of claim 3 further comprising a porous substrate layer in adhesive contact with the hot-melt adhesive coating layer.

12. The laminate of claim 3 wherein the microporous film has an L value of at least 75 at the points of adhesive contact and an L value of at least 80 in the areas not in contact with adhesive.

13. The laminate of claim 1 wherein the hot-melt adhesive further comprises 0 to 50 parts of a filler to 100 parts of the adhesive.

14. The laminate of claim 1 wherein the laminate comprises a disposable absorbent article comprising the microporous film adhered to an absorbent batt structure via the hot-melt adhesive.

15. The laminate of claim 1 wherein the plasticizer comprises 0 to 20 parts of a plasticizing oil having an average molecular weight of less than 500.

16. The laminate of claim 8 wherein the adhesive composition comprises 0 to 35 parts of a plasticizer having an average molecular weight of at least 1000.

17. The laminate of claim 1 wherein the laminate further comprises a porous substrate layer in adhesive contact with the hot-melt adhesive coating layer.

18. The laminate of claim 17 wherein the T peel adhesion of the microporous film to the porous substrate is at least 30 g/25 mm after 15 days of heat aging and 2,000 grams adhesive rolldown to the laminate when formed.

19. The laminate of claim 18 wherein the T peel is at least 50 g/25 mm.

20. The laminate of claim 16 wherein the plasticizer comprises a microcrystalline wax.

21. The laminate of claim 15 wherein the plasticizer comprises a polybutene oil.

22. The laminate of claim 16 wherein the plasticizer comprises a polyethylene wax.

23. The laminates of claim 1 wherein the adhesive further comprises 0.01 to 5 parts of a nucleating agent.

24. The laminate of claim 23 wherein the nucleating agent is less than 1 part.

25. The laminate of claim 1 wherein the adhesive polymer is a polybutylene copolymer having 2 to 13 mole percent of the alpha olefin comonomer.

26. The laminate of claim 25 wherein the alpha olefin comonomer is an ethylene monomer.

27. The laminate of claim 1 wherein the laminate further comprises a substrate layer.

28. The laminate of claim 26 wherein the laminate is point or pattern embossed.

* * * * *